US011682491B2

(12) United States Patent
Nagai et al.

(10) Patent No.: US 11,682,491 B2
(45) Date of Patent: Jun. 20, 2023

(54) MEDICAL INFORMATION PROCESSING APPARATUS AND MEDICAL INFORMATION PROCESSING METHOD

(71) Applicant: CANON MEDICAL SYSTEMS CORPORATION, Otawara (JP)

(72) Inventors: Yasuhito Nagai, Nasushiobara (JP); Keita Mitsumori, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 332 days.

(21) Appl. No.: 16/903,604

(22) Filed: Jun. 17, 2020

(65) Prior Publication Data
US 2020/0402663 A1 Dec. 24, 2020

(30) Foreign Application Priority Data
Jun. 18, 2019 (JP) .............................. JP2019-113084

(51) Int. Cl.
*G16H 50/20* (2018.01)
*G06N 20/00* (2019.01)
*G16H 50/70* (2018.01)

(52) U.S. Cl.
CPC ............. *G16H 50/20* (2018.01); *G06N 20/00* (2019.01); *G16H 50/70* (2018.01)

(58) Field of Classification Search
CPC ......... G16H 10/00–80/00; G06N 3/00–99/007
See application file for complete search history.

(56) References Cited

U.S. PATENT DOCUMENTS

| 8,768,870 B1 | 7/2014 | Corrado et al. |
| 9,928,342 B1 * | 3/2018 | LaBorde ............... A61B 5/6852 |
| 10,810,512 B1 * | 10/2020 | Wubbels ................ G16H 50/20 |
| 11,164,093 B1 * | 11/2021 | Zappella ................ G06N 5/045 |
| 11,250,937 B2 * | 2/2022 | Malvankar ............ H04L 9/3239 |

(Continued)

FOREIGN PATENT DOCUMENTS

| CN | 109800048 A * | 5/2019 | |
| CN | 112189235 A * | 1/2021 | ........... G06K 9/6202 |

(Continued)

OTHER PUBLICATIONS

Mohri, M. et al., "Agnostic Federated Learning," arXiv:1902.00146v1 [cs.LG], Feb. 1, 2019, pp. 1-30.

*Primary Examiner* — Jonathon A. Szumny
(74) *Attorney, Agent, or Firm* — Oblon, McClelland, Maier & Neustadt, L.L.P.

(57) ABSTRACT

A medical information processing apparatus according to an embodiment includes a processing circuitry. The processing circuitry is configured: to evaluate each of a plurality of machine learning models on a basis of an output result from each of the machine learning models obtained by inputting mutually the same medical data to the machine learning models and success/failure judgment results on the output results, the plurality of machine learning models being created from a plurality of pieces of medical data and either created from at least partially mutually-different medical data or created under mutually-different parameter conditions; and to cause results of the evaluation on the machine learning models to be displayed in such a manner that comparison is possible.

11 Claims, 8 Drawing Sheets

(56) References Cited

U.S. PATENT DOCUMENTS

| | | | |
|---|---|---|---|
| 2014/0101080 A1* | 4/2014 | Lee | G16H 30/40 706/12 |
| 2014/0188517 A1* | 7/2014 | Arai | G16H 10/60 705/3 |
| 2016/0070879 A1 | 3/2016 | Hatlelid et al. | |
| 2017/0193655 A1* | 7/2017 | Madabhushi | G06T 7/0012 |
| 2018/0330237 A1* | 11/2018 | Yoshiyama | G06F 16/838 |
| 2018/0366222 A1* | 12/2018 | Tang | G06N 3/006 |
| 2019/0124479 A1* | 4/2019 | Garg | G16H 40/63 |
| 2019/0392351 A1* | 12/2019 | Zuluaga | G06N 20/20 |
| 2020/0012962 A1* | 1/2020 | Dent | G06F 9/5011 |
| 2020/0015683 A1* | 1/2020 | Katsuki | A61B 5/6891 |
| 2020/0050892 A1* | 2/2020 | Conroy | G06K 9/6262 |
| 2020/0117490 A1* | 4/2020 | Sengupta | G06N 5/04 |
| 2020/0302234 A1* | 9/2020 | Walters | G06K 9/6276 |
| 2020/0311615 A1* | 10/2020 | Jammalamadaka | G06N 20/20 |
| 2020/0320349 A1* | 10/2020 | Yu | H04L 9/3239 |
| 2020/0320381 A1* | 10/2020 | Venkatraman | G06Q 10/067 |
| 2020/0334566 A1* | 10/2020 | Vianu | G06N 3/0454 |
| 2020/0334570 A1* | 10/2020 | Franklin | G06N 20/00 |
| 2020/0365255 A1* | 11/2020 | Hayashitani | G16H 50/30 |

FOREIGN PATENT DOCUMENTS

| | | | | |
|---|---|---|---|---|
| EP | 3101599 A2 * | 12/2016 | | G06N 5/043 |
| EP | 3182283 A1 * | 6/2017 | | G06F 16/22 |
| JP | 2017-527399 A | 9/2017 | | |
| WO | WO-2016152053 A1 * | 9/2016 | | G06N 5/048 |
| WO | WO-2017075657 A1 * | 5/2017 | | G06N 3/02 |
| WO | WO-2018058189 A1 * | 4/2018 | | G06N 20/00 |
| WO | WO-2018125264 * | 7/2018 | | G06Q 10/04 |
| WO | WO-2019211308 A1 * | 11/2019 | | G16H 50/20 |

* cited by examiner

| No | LOCAL MODEL (FIRST GENERATION) | LOCAL MODEL (SECOND GENERATION) | GLOBAL MODEL (FIRST GENERATION) |
|---|---|---|---|
| 0001 | 1 | 0 | 1 |
| 0002 | 0 | 1 | 1 |
| ⋮ | ⋮ | ⋮ | ⋮ |
| 1000 | 0 | 1 | 1 |

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2019-113084, filed on Jun. 18, 2019; the entire contents of which are incorporated herein by reference.

FIELD

Embodiments described herein relate generally to a medical information processing apparatus and a medical information processing method.

BACKGROUND

In recent years, the artificial intelligence (AI) (machine learning) technology has been used in various systems and has also increasingly been applied to the medical industry. For example, if in specific medical cases, a known machine learning model is capable of detecting abnormality locations more quickly and more precisely than interpreting doctors.

A plurality of pieces of medical data are used for creating a machine learning model. Because the number of pieces of data increases day by day, the machine learning model is updated with the most up-to-date medical data. Further, it is expected that, to increase the number of pieces of data (the number of samples), some machine learning models may be created by using medical data from more than one hospital.

In that situation, for example, it is possible to create a plurality of machine learning models having mutually-different conditions, by varying conditions of the medical data to be used in machine learning processes or parameter conditions such as hyperparameters related to the creation of the machine learning models; however, one machine learning model will usually be used. It is not easy to compare capabilities of the plurality of machine learning models. For this reason, there is a demand for a technique that facilitates the machine learning model selecting process.

DETAILED DESCRIPTION

A medical information processing apparatus according to an embodiment includes a processing circuitry. The processing circuitry is configured: to evaluate each of a plurality of machine learning models on a basis of an output result from each of the machine learning models obtained by inputting mutually the same medical data to the machine learning models and success/failure judgment results on the output results, the plurality of machine learning models being created from a plurality of pieces of medical data and either created from at least partially mutually-different medical data or created under mutually-different parameter conditions; and to cause results of the evaluation on the machine learning models to be displayed in such a manner that comparison is possible.

Exemplary embodiments of a medical information processing apparatus and a medical information processing method will be explained below, with reference to the accompanying drawings.

Figure 1:
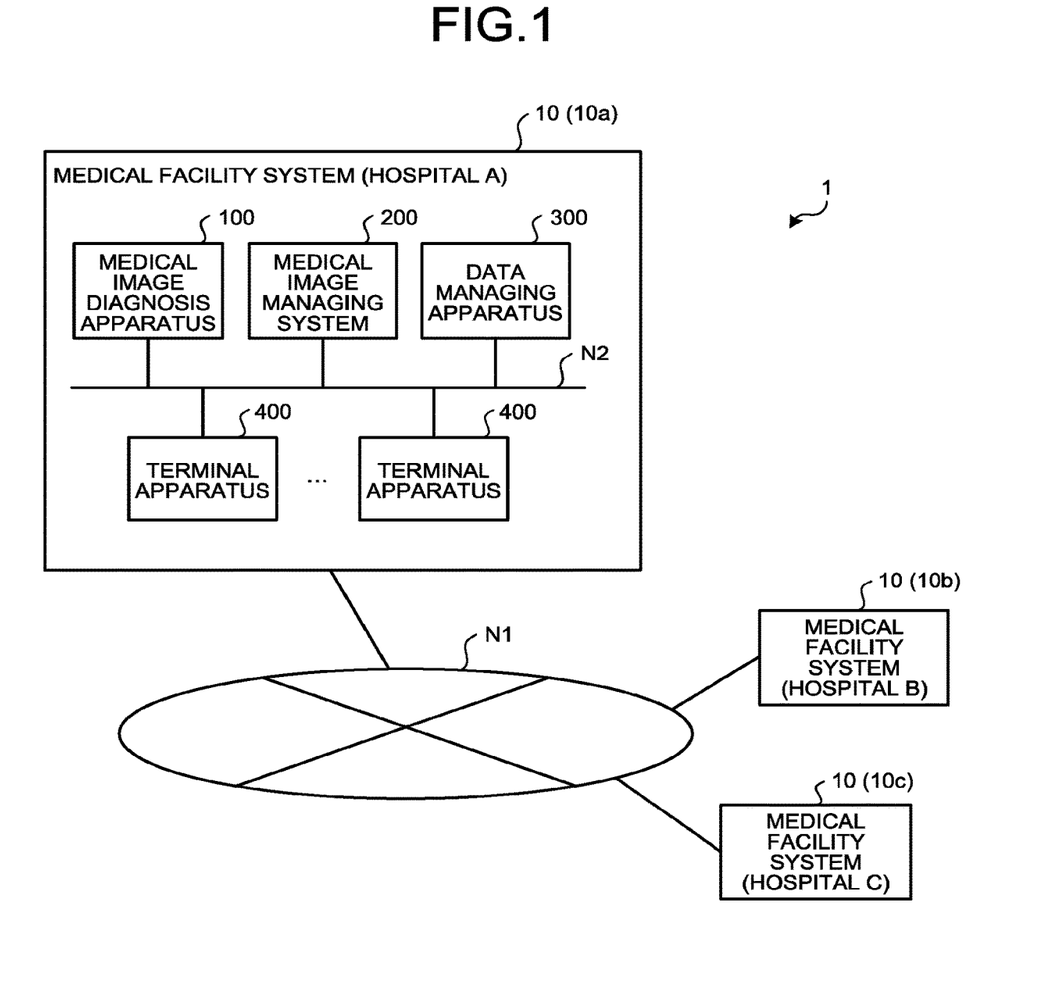
FIG. 1 is a diagram illustrating an exemplary configuration of a medical information system according to an embodiment.

FIG. 1 is a diagram illustrating an exemplary configuration of a medical information system according to an embodiment. As illustrated in FIG. 1, a medical information system 1 includes a plurality of medical facility systems 10 (10a to 10c). The medical facility systems 10 are connected to one another so as to be able to communicate via a network N1 realized with an intranet, a dedicated communication line, or the like. The number of medical facility systems 10 connected to the network N1 is not particularly limited.

Each of the medical facility systems 10 is a system provided in a medical facility such as a hospital. In the example in FIG. 1, the medical facility system 10a is a medical facility system of hospital A. The medical facility system 10b is a medical facility system of hospital B. The medical facility system 10c is a medical facility system of hospital C.

Each of the medical facility systems 10 includes, for example, a medical image diagnosis apparatus 100, a medical image managing system 200, a data managing apparatus 300, terminal apparatus 400, and the like. The medical image diagnosis apparatus 100, the medical image managing system 200, the data managing apparatus 300, and the terminal apparatus 400 are connected so as to be able to communicate via a network N2 realized with a Local Area Network (LAN) or the like. Further, via a network device such as a router, the network N2 is connected to the network N1.

The medical image diagnosis apparatus 100 is an apparatus configured to perform a medical examination by imaging an examined subject (hereinafter "patient") or the like. Examples of the medical image diagnosis apparatus 100 include an X-ray computed tomography apparatus, an X-ray diagnosis apparatus, a magnetic resonance imaging apparatus, a nuclear medicine diagnosis apparatus, and an ultrasound diagnosis apparatus.

By performing the medical examination, the medical image diagnosis apparatus 100 is configured to generate medical image data. Example of the medical image data include X-ray CT image data, X-ray image data, MRI image data, nuclear medicine image data, and ultrasound image data. For example, the medical image data is generated in a format compliant with a Digital Imaging and Communication in Medicine (DICOM) standard. The medical image diagnosis apparatus 100 is configured to transmit the generated image data to the medical image managing system 200.

For example, the medical image managing system 200 is a Picture Archiving and Communication System (PACS) and is configured to store therein and manage the medical image data generated by the medical image diagnosis apparatus 100.

The data managing apparatus 300 is an example of the medical information processing apparatus. The data managing apparatus 300 is configured to manage various types of data used in the medical facility system 10. For example, the data managing apparatus 300 stores therein local models LM and global models GM (see FIG. 2; explained later) as machine learning models (which hereinafter may be referred to as "models") related to assisting diagnosing processes performed by medical providers such as medical doctors. Further, the data managing apparatus 300 is configured to acquire diagnosis results diagnosed by using the models from any of the terminal apparatus 400. For example, the data managing apparatus 300 is realized by using a computer device such as a workstation or a server apparatus.

Each of the terminal apparatus 400 is a terminal device used by a medical provider such as a medical doctor. Each of the terminal apparatus 400 is configured to perform various processes in response to operations performed by the medical provider. More specifically, each of the terminal apparatus 400 is configured to assist diagnosing processes such as detecting an abnormality location, by analyzing the medical image data managed by the medical image managing system 200, while using the models managed by the data managing apparatus 300. For example, each of the terminal apparatus 400 is realized by using a computer device such as a personal computer or a tablet terminal.

Figure 2:
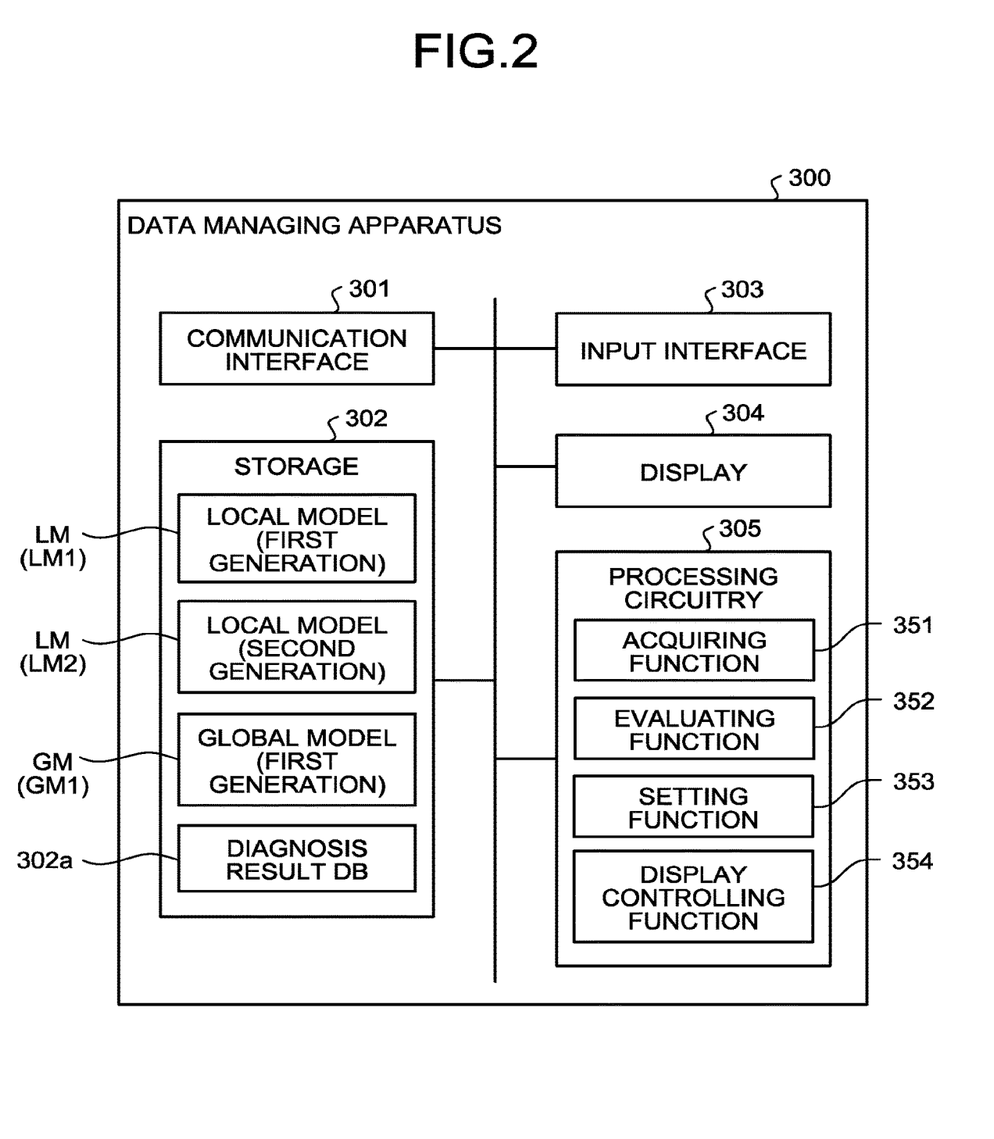
FIG. 2 is a diagram illustrating an exemplary configuration of a data managing apparatus according to the embodiment.

Next, a configuration of the data managing apparatus 300 presented above will be explained. FIG. 2 is a diagram illustrating an exemplary configuration of the data managing apparatus 300. As illustrated in FIG. 2, the data managing apparatus 300 includes a communication interface 301, a storage 302, an input interface 303, a display 304, and a processing circuitry 305.

The communication interface 301 is connected to the processing circuitry 305 and is configured to control transfer of various types of data and communication performed between the data managing apparatus 300 and external apparatuses. For example, the communication interface 301 is realized by using a network card, a network adaptor, a Network Interface Controller (NIC), or the like.

The storage 302 is connected to the processing circuitry 305 and is configured to store therein various types of data and various types of programs. More specifically, the storage 302 is configured to store therein the local models LM and the global models GM as models related to assisting the diagnosing processes performed by the medical doctors. Further, the storage 302 holds therein a diagnosis result database (DB) 302a for storing diagnosis result data transmitted thereto from any of the terminal apparatus 400. For example, the storage 302 is realized by using a semiconductor memory element such as a Random Access Memory (RAM) or a flash memory, or a hard disk, an optical disk, or the like. The storage 302 is an example of a means for realizing a storage unit.

In this situation, the local models LM are each an example of the first machine learning model and a model created by using data from the host medical facility (e.g., hospital A). More specifically, each of the local models LM is created by learning a relationship between medical image data obtained by the medical image diagnosis apparatus 100 provided in the host medical facility and results of diagnoses (designation of abnormality locations or the like) made from the medical image data at the host medical facility. Upon receipt of an input of medical image data, each of the local models LM is configured to estimate (detect) an abnormality location, a lesion location, or the like rendered in the medical image data and to output an estimated result.

Further, the storage 302 is configured to store therein the local models LM in correspondence with the generations thereof. A local model LM1 denotes a local model LM of the first generation. A local model LM2 denotes a local model LM of the second generation. Further, conditions of data sets (medical image data and diagnosis results) used for creating the local models LM are different among different generations. For example, let us discuss an example in which the number of diagnosis that have so far been made at the host medical facility is 1,000, and a new local model LM is created for every 500 diagnoses. In this situation, the local model LM1 is created from the data set of the 1st to the 500th diagnoses. The local model LM2 is created from the data set of the 1st to the 1,000th diagnoses (or the 500th to the 1,000th diagnoses). In other words, the local model LM1 and the local model LM2 are created from the data sets that are partially or entirely different from each other.

In this situation, the method for creating the local models LM is not particularly limited and may be created by using any of publicly-known techniques. Further, the local models LM may be created by the data managing apparatus 300 at the host medical facility or may be created by another apparatus at the host medical facility. For example, when the data managing apparatus 300 is configured to create the local models LM, the data managing apparatus 300 may create the local models LM by using the medical image data stored in the medical image managing system 200 and the diagnosis result data stored in the diagnosis result DB 302a.

Further, the global models GM are each an example of the second machine learning model and a model created by using data from a plurality of medical facilities. For example, each of the global models GM is created by learning a relationship between medical image data obtained by the medical image diagnosis apparatuses 100 at the host medical facility (e.g., hospital A) and other medical facilities (e.g., hospitals B and C) and results of diagnoses (designations of abnormality locations or the like) made from the medical image data at these medical facilities. Similarly to the local models LM, upon receipt of an input of medical image data, each of the global models GM is configured to estimate (detect) an abnormality location, a lesion location, or the like rendered in the medical image data and to output an estimated result.

Further, the storage 302 is configured to store therein the global models GM in correspondence with the generations thereof. A global model GM1 denotes a global model GM of the first generation. In this situation, data sets (medical image data and diagnosis results) used for creating the global models GM of generations are different among different generations, similarly to the local models LM. In other words, the global models GM are created from data sets that are partially or entirely different among the different generations. Further, the local models LM and the global models GM are created from data sets that are partially or entirely different from each other.

In this situation, the method for creating the global models GM is not particularly limited and may be created by using any of publicly-known techniques. Further, the global models GM may be created by a data managing apparatus 300 or the like at the respective medical facilities or may be created by the data managing apparatus 300 at a single representative medical facility. For example, when a data managing apparatus 300 is configured to create a global models GM, the data managing apparatus 300 may create the global model GM by using the medical image data stored in the medical image managing system 200 at each of the medical facilities and the diagnosis result data stored in the diagnosis result DB 302a at each of the medical facilities.

Among the local models LM and the global models GM described above, the data managing apparatus 300 is configured supply each of the terminal apparatus 400 with one of the models (of one generation) set as a currently-used model. In each of the terminal apparatus 400, according to an operation performed by a medical provider such as a medical doctor, medical image data of a patient to be diagnosed that is obtained from the medical image managing system 200 is input to the currently-used model. The currently-used model is configured to estimate an abnormality location or the like rendered in the medical image data and to output the estimated result to the display device or the like of the terminal device 400.

A medical provider who operates any of the terminal apparatus 400 is able to make observations and diagnoses from the medical image data, by referring to the estimated result from the currently-used model. In this manner, the models managed by the data managing apparatuses 300 are used for assisting diagnosing processes performed by medical doctors. When a medical doctor operating any of the terminal apparatus 400 has made a diagnosis by using the currently-used model, he/she inputs information indicating whether the estimated result is correct or incorrect, and the like, together with the diagnosis result. Further, the input diagnosis result is transmitted to the data managing apparatus 300 as diagnosis result data and is thereby stored into the diagnosis result DB 302a of the data managing apparatus 300.

In this situation, for example, the diagnosis result data includes: a patient ID identifying the patient subject to the diagnosing process, an image ID identifying the medical image data, a model ID identifying the used model (the currently-used model), the estimated result from the currently-used model, the diagnosis result from the medical doctor, and the correct/incorrect information indicating whether the estimated result from the currently-used model is correct or incorrect. Of these pieces of information, for example, the diagnosis result from the medical doctor and the correct/incorrect information are input by the medical doctor.

The information included in the diagnosis result data is not limited to the examples above, and other types of information may be included. For instance, when a medical provider has input a comment or has appended a flag to indicate importance or the like, the diagnosis result data may include information such as the text of the input comment or the flag (hereinafter "seriousness flag"). Further, the diagnosis result data may include, for example, a medical doctor ID identifying the medical doctor who made the diagnosis, or the like. Further, the diagnosis result data may be configured not to explicitly include the correct/incorrect information. In that situation, the correct/incorrect information may be configured so as to be derived from the estimated result from the currently-used model and the diagnosis result from the medical doctor.

The input interface 303 is connected to the processing circuitry 305 and is configured to receive operations to input various types of instructions and various types of information from an operator. More specifically, the input interface 303 is configured to convert the input operations received from the operator into electrical signals and to output the electrical signals to the processing circuitry 305. For example, the input interface 303 is realized by using a trackball, a switch button, a mouse, a keyboard, a touchpad on which input operations are performed by touching an operation surface thereof, a touch screen in which a display screen and a touchpad are integrally formed, a contactless input circuit using an optical sensor, an audio input circuit, and/or the like. The input interface 303 does not necessarily have to include physical operation component parts such as a mouse, a keyboard, and/or the like. Possible examples of the input interface 303 include an electric signal processing circuit configured to receive an electric signal corresponding to an input operation from an external input device provided separately from the apparatus and to output the received electric signal to a controlling circuit.

The display 304 is connected to the processing circuitry 305 and is configured to display various types of information and various types of images. More specifically, the display 304 is configured to convert data of the various types of information and the various types of images sent thereto from the processing circuitry 305 into display-purpose electrical signals and to output the display-purpose electrical signals. For example, the display 304 is realized by using a liquid crystal monitor, a Cathode Ray Tube (CRT) monitor, a touch panel, or the like.

The processing circuitry 305 is configured to control constituent elements of the data managing apparatus 300, in accordance with the input operations received from the operator via the input interface 303. More specifically, the processing circuitry 305 reads the medical data from the storage 302 and to display the medical data on the display 304. For example, the processing circuitry 305 is realized by using a processor.

Further, the data managing apparatus 300 has a function for assisting the model selecting process described above. More specifically, the data managing apparatus 300 includes an acquiring function 351, an evaluating function 352, a setting function 353, and a display controlling function 354. The evaluating function 352 is an example of an evaluating unit. The display controlling function 354 is an example of a display controlling unit.

The acquiring function 351 is configured to acquire (obtain) the diagnosis result data transmitted from each of the terminal apparatus 400. Further, the acquiring function 351 is configured to store the acquired diagnosis result data into the diagnosis result DB 302a.

On the basis of the diagnosis result data stored in the diagnosis result DB 302a, the evaluating function 352 is configured to evaluate capabilities of each of the models stored in the storage 302. More specifically, on the basis of the diagnosis results from medical doctors and the correct/incorrect information included in the diagnosis result data, the evaluating function 352 is configured to evaluate estimated results from the currently-used models and currently-not-used models by using an index such as a ratio of correct incidents or the like.

For example, let us discuss an example in which, with respect to the medical image data input to the currently-used model (e.g., the local model LM1), a piece of diagnosis result data has been stored in the diagnosis result DB 302a. In this situation, on the basis of the correct/incorrect information and the model ID included in the diagnosis result data, the evaluating function 352 judges whether or not the estimated result from the model (the currently-used model)

corresponding to the model ID is correct. In this situation, when the estimated result from the currently-used model is correct, the evaluating function 352 increments the number of correct incidents of the currently-used model by 1.

Further, the evaluating function 352 is configured to read medical image data corresponding to the image ID included in diagnosis result data Dl from the medical image managing system 200 and to input the medical image data to each of the currently-not-used models (e.g., the local model LM2 and the global model GM1). Further, the evaluating function 352 is configured to compare the diagnosis result from the medical provider included in the diagnosis result data of the currently-used model, with the estimated result output from each of the currently-not-used models and to judge whether or not the estimated results are correct.

More specifically, when determining that the estimated result from any of the currently-not-used models is the same as the diagnosis result from the medical provider, the evaluating function 352 determines that the estimated result from the currently-not-used model is correct. On the contrary, when determining that the estimated result from any of the currently-not-used models is different from the diagnosis result from the medical provider, the evaluating function 352 determines that the estimated result from the currently-not-used models is incorrect. In this situation, when the estimated result from any of the currently-not-used models is correct, the evaluating function 352 increments the number of correct incidents of the pertinent currently-not-used model by 1.

Figure 3:
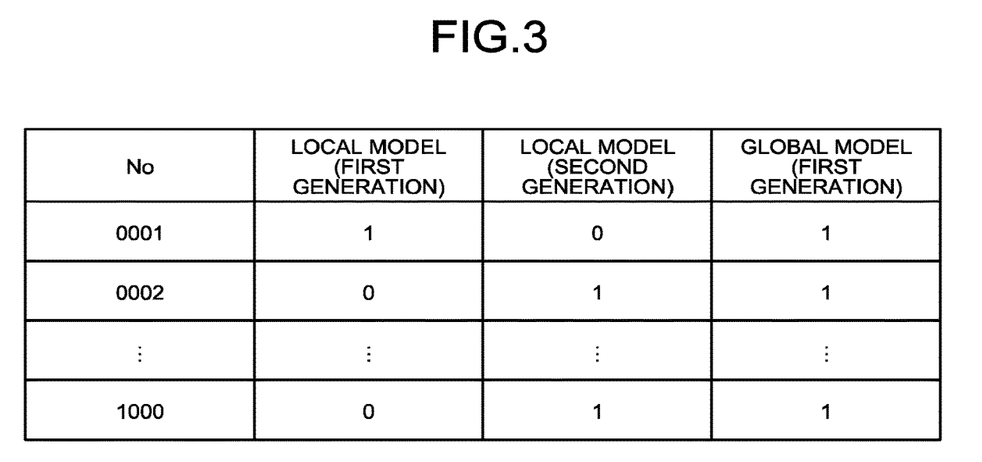
FIG. 3 is a table for explaining operations of an evaluating function according to the embodiment.

FIG. 3 is a table for explaining operations of the evaluating function 352 and illustrates an example of the method for counting the number of correct incidents. In FIG. 3, in the column "No. (number)" are the numbers used for counting the diagnoses. For example, let us assume that, for the diagnosis numbered "0001", the models exhibited estimated results as illustrated in FIG. 3. In this situation, "1" denotes that the estimated result was correct, whereas "0" denotes that the estimated result was incorrect. The evaluating function 352 judges whether or not the estimated result from each of the models is correct, every time a diagnosis is made by using the currently-used model and counts the number of correct incidents on the basis of the judgment results.

Further, for example, when the number of diagnoses reaches 1,000, the evaluating function 352 calculates the ratio of the correct incidents to the number of diagnoses, as a ratio of correct incidents. The evaluation results of the models calculated by the evaluating function 352 are saved in the storage 302 or the like so as to be kept in correspondence with the model IDs of the respective models.

As for the method for evaluating the models, the ratio of the correct incidents does not necessarily have to be used, and other evaluation indices may be used. For example, the machine learning models may be evaluated by using a statistical evaluation index used in the field of machine learning and the like, such as a recall factor, a precision factor, an F value, or a variance. Further, another mode (see FIG. 3) is also acceptable in which, when a model of a new generation has been created, it is judged whether or not the result is correct by retroactively using the diagnosis result data from the past prior to the creation of the model.

Further, the timing with which the evaluating process is started by the evaluating function 352 is not particularly limited and may arbitrarily be set. For example, the evaluating function 352 may be configured to start the evaluating process every time a predetermined number (e.g., 100) of pieces of diagnosis result data have been registered. Alternatively, the evaluating function 352 may be configured to start the evaluating process when being instructed to update the evaluation results via the input interface 303 or the like.

Further, although the example was explained above in which the evaluating function 352 is configured to automatically judge whether the result from each of the currently-not-used models is correct or incorrect, possible embodiments are not limited to this example. Another mode is also acceptable in which medical providers such as medical doctors manually make the judgements.

Returning to the description of FIG. 2, the display controlling function 354 is configured to control a screen displayed on the display 304. More specifically, on the basis of the evaluation results or the like calculated by the evaluating function 352, the display controlling function 354 is configured to cause the display 304 to display a screen (hereinafter, "model comparison screen") that makes it possible to compare the capabilities of the models.

Figure 4:
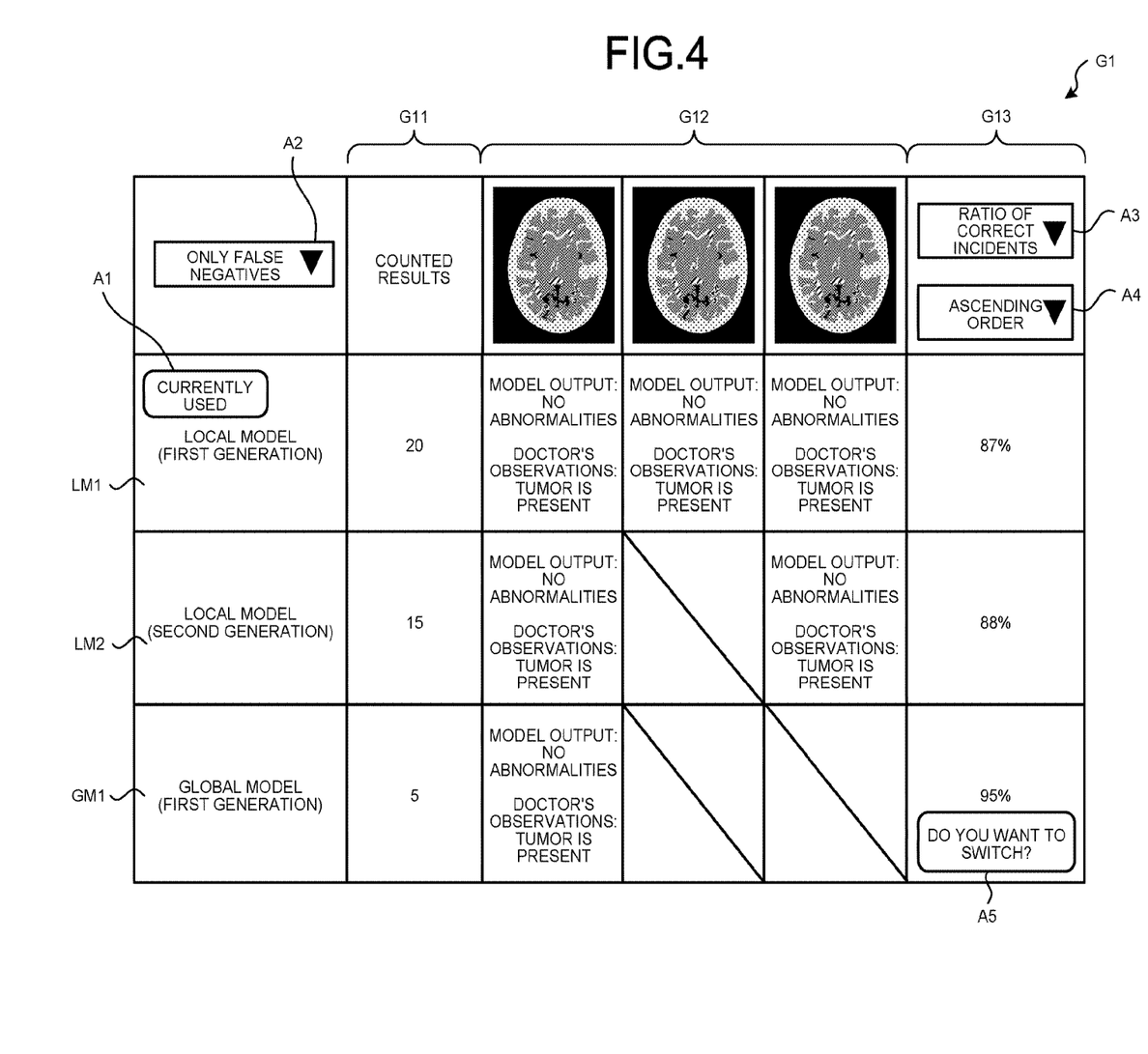
FIG. 4 is a drawing illustrating an example of a model comparison screen displayed by a display controlling function according to the embodiment.

FIG. 4 is a drawing illustrating an example of the model comparison screen displayed by the display controlling function 354. As illustrated in FIG. 4, a model comparison screen G1 displays each of the models stored in the storage 302 in correspondence with various types of information related to the model. FIG. 4 illustrates the example in which the local model LM1, the local model LM2, and the global model GM1 described above are displayed. The information about these models is displayed in counted result display sections G11, detail display sections G12, and evaluation display sections G13.

In this situation, the display controlling function 354 is configured to display the currently-used model (e.g., the local model LM1) with an emphasis, so as to be distinguishable from the currently-not-used models. More specifically, by bringing a marker A1 indicating a currently-used model into correspondence therewith, the display controlling function 354 displays the local model LM1 with an emphasis, so as to be distinguishable from the local model LM2 and the global model GM1.

Further, in FIG. 4, an operator A2 is an operator for selecting a counting type. More specifically, by using a pull-down menu style or the like, the operator makes it possible to select one of a plurality of counting types. Examples of the counting types include "all", "only correct incidents", "only false negatives", and "only false positives". By operating the operator A2, the user of the data managing apparatus 300 is able to select one of the counting types.

When one of the counting types has been selected via the operator A2, the display controlling function 354 displays, in the counted result display section G11 of the pertinent model, the number of diagnoses corresponding to the condition of the selected counting type, among the diagnoses made by using each of the models. In this situation, it is desirable when the number of diagnoses includes not only the number of diagnoses made by medical doctors while actually using the currently-used model, but also the number of incidents diagnosed (judged correct or incorrect) by the evaluating function 352 while using the currently-not-used models.

For example, when the counting type "all" is selected, the display controlling function 354 displays the number of pieces of diagnosis result data including the model ID of each of the models so as to be kept in correspondence with the pertinent model. In another example, when the counting type "only correct incidents" is selected, the display controlling function 354 displays, among the diagnoses made by using each of the models, the number of pieces of diagnosis result data set with an evaluation result "correct", so as to be kept in correspondence with the pertinent model.

In yet another example, when the counting type "only false negatives" is selected, the display controlling function 354 displays, among the diagnoses made by using each of the models, the number of pieces of diagnosis result data in which the diagnosis result data from the model set therewith indicates negative (e.g., no abnormalities), but in which the diagnosis result from a medical provider indicates positive (e.g., a tumor is present), so as to be kept in correspondence with the pertinent model. FIG. 4 illustrates an example of the display presented when the counting type "only false negatives" is selected. In the present example, the counted result display sections G11 display that the numbers of pieces of diagnosis result data corresponding to "only false negatives" are: 20 for the local model LM1; 15 for the local model LM2; and 5 for the global model GM1.

Possible counting types are not limited to those in the above example, and other conditions may be selectable. For instance, one of the selectable conditions may be extracting only such pieces of diagnosis result data to which the seriousness flag is appended. As another example, the user may be able to select a medical doctor ID. As yet another example, another selectable conditions may be extracting such pieces of diagnosis result data that correspond to the same image ID and are indicated as "incorrect" in the correct/incorrect information of the currently-used model, but are indicated as "correct" in the correct/incorrect information of one or more currently-not-used models.

Further, the display controlling function 354 is configured to display, in the detail display sections G12, details of the pieces of diagnosis result data corresponding to the condition of the counting type. For example, in FIG. 4, the detail display sections G12 display the details of the diagnosis result data corresponding to the condition of the counting type "only false negatives". In the present example, as the details of the diagnosis result data, estimated results from the models (model output) and diagnosis results from the medical doctors (doctor's observations) are displayed. In the detail display sections G12, the details of the diagnoses displayed in mutually the same column are the details of the diagnoses from each of the models corresponding to the medical image data displayed in the upper section of the detail display sections G12. Further, when there is no diagnosis result data such as evaluation results made by the evaluating function 352 for the currently-not-used models, the sections for the details of diagnoses are left empty.

Further, the display controlling function 354 displays, in the evaluation display sections G13, evaluation results made on the models by the evaluating function 352. In the present example, an operator A3 for the evaluation display sections G13 is an operator for selecting an evaluation index. More specifically, by using a pull-down menu style or the like, the operator A3 makes it possible to select one of a plurality of evaluation indices. Examples of the evaluation indices include a ratio of correct incidents, a recall factor, a precision factor, an F value, and a variance. The user of the data managing apparatus 300 is able to select one of the evaluation indices by operating the operator A3.

When one of the evaluation indices has been selected via the operator A3, the display controlling function 354 displays the evaluation results made by the evaluating function 352 while using the selected evaluation index, so as to be kept in correspondence with the respective models. FIG. 4 illustrates an example of the display presented when the evaluation index "ratio of correct incidents" is selected. In the present example, the evaluation display sections G13 display that the ratio of correct incidents for the local model LM1 is 87%; the ratio of correct incidents for the local model LM2 is 88%; and the ratio of correct incidents for the global model GM1 is 95%.

Further, an operator A4 for the evaluation display sections G13 is an operator for switching the display order of the models while using the values of the evaluation results as a reference. More specifically, by using a pull-down menu style or the like, the operator A4 makes it possible to select one of the ascending order and the descending order. By operating the operator A4, the user of the data managing apparatus 300 is able to select one of the ascending order and the descending order, as the display order of the models.

When one of the ascending order and the descending order has been selected via the operator A4, the display controlling function 354 switches the display order of the models into the selected one of the ascending order and the descending order, on the basis of the evaluation results of the models according to the evaluation index selected while using the operator A4. FIG. 4 illustrates an example of the display presented when the "ascending order" is selected in which the models are displayed in the ascending order of the "ratios of correct incidents" set as the evaluation index.

Further, when a highly-evaluated model having the highest evaluation among the evaluation results of the models is a model other than the currently-used model, the display controlling function 354 is configured to display proposal information A5 including a message that proposes switching the currently-used model, so as to be kept in correspondence with the highly-evaluated model. In the example in FIG. 4, because the model having the highest "ratio of correct incidents" is the global model GM1, which is not the currently-used model, the proposal information A5 is displayed in the evaluation display section G13 of the global model GM1.

As explained above, the display controlling function 354 is configured to display, on the model comparison screen G1, the evaluation results and the like of the models in such a manner that comparison is possible. As a result, by using the data managing apparatus 300, it is possible to easily compare the capabilities and the like of the models, such as the evaluation results between the currently-used model and the currently-not-used models. It is therefore possible to assist the model selecting process.

The proposal information A5 described above may be configured to function as an operator for switching the currently-used model. In this situation, upon receipt of an operation performed on the proposal information A5 via the input interface 303 or the like, the setting function 353 is configured to set the model kept in correspondence with the proposal information A5 as a currently-used model. For example, in the example in FIG. 4, when the proposal information A5 is operated, the setting function 353 switches the currently-used model from the local model LM1 to the global model GM1. With this arrangement, the user of the data managing apparatus 300 is able to easily switch the currently-used model. It is therefore possible to enhance convenience related to the model selecting process.

Figure 5:
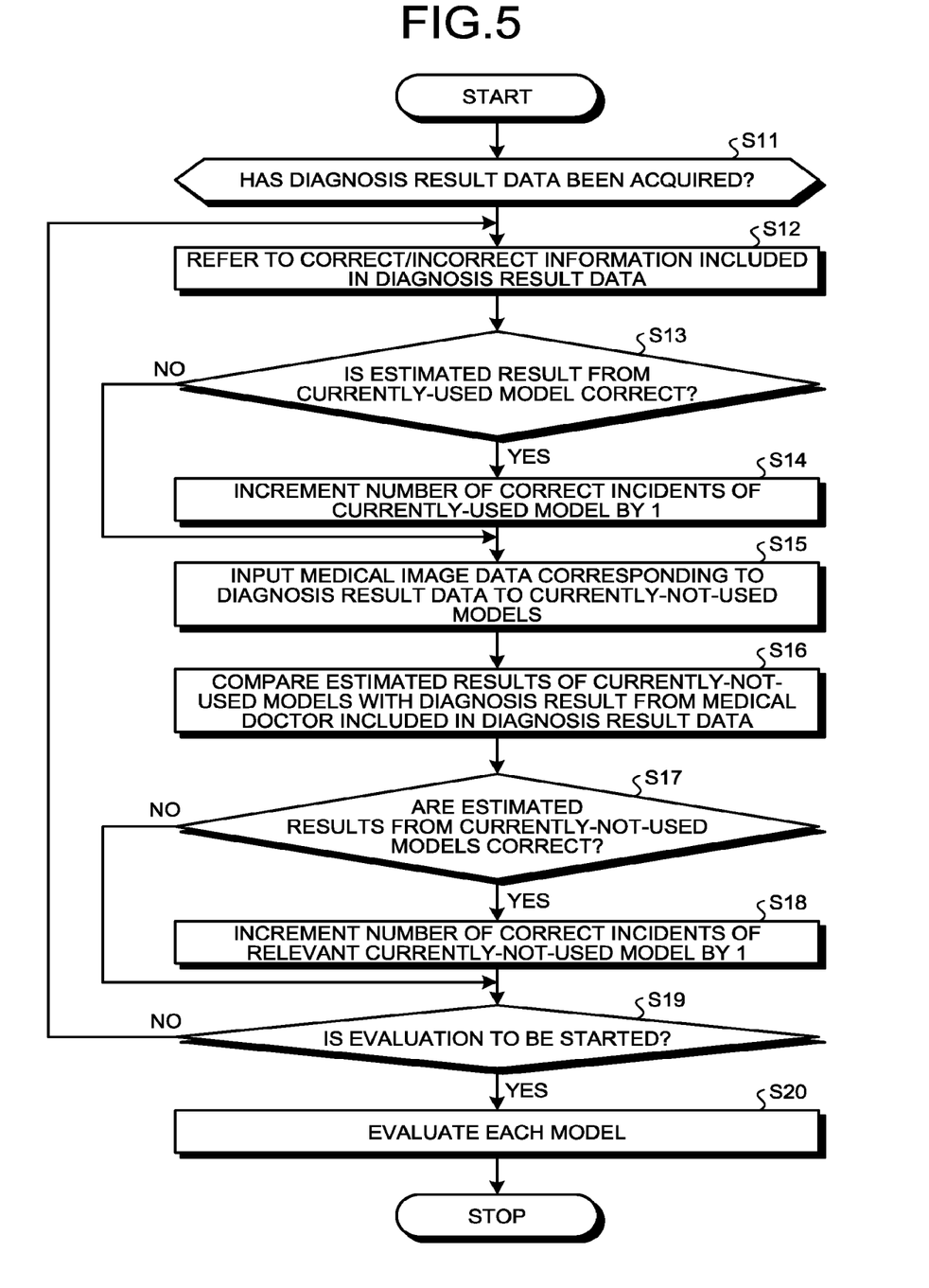
FIG. 5 is a flowchart illustrating an example of an evaluating process performed by the data managing apparatus according to the embodiment.

Next, an example of operations performed by the data managing apparatus 300 will be explained, with reference to FIGS. 5 and 6. FIG. 5 is a flowchart illustrating an example of the evaluating process performed by the data managing apparatus 300. As a premise of the present process, it is assumed that the plurality of models including a currently-used model have already been created in advance.

First, the acquiring function 351 acquires diagnosis result data of diagnoses made by using the currently-used model from each of the terminal apparatus 400 (step S11). The acquired diagnosis result data is registered into the diagnosis result DB 302a.

By referring to the correct/incorrect information included in the newly-acquired diagnosis result data in the diagnosis result DB 302a (step S12), the evaluating function 352 judges whether or not the estimated result from the currently-used model is correct (step S13).

When the estimated result from the currently-used model is correct (step S13: Yes), the evaluating function 352 increments the number of correct incidents of the currently-used model by 1 (step S14) and proceeds to step S15. On the contrary, when the estimated result from the currently-used model is incorrect (step S13: No), the evaluating function 352 immediately proceeds to step S15. Alternatively, in a mode in which the number of incorrect incidents is also counted, the process may proceed to step S15 after the number of incorrect incidents of the currently-used model is counted.

Subsequently, the evaluating function 352 reads the medical image data corresponding to the image ID included in the diagnosis result data from the medical image managing system 200 and inputs the read medical image data to each of the currently-not-used models other than the currently-used model designated with the model ID (step S15). After that, the evaluating function 352 compares the diagnosis result included in the diagnosis result data from the currently-used model with the estimated result output from each of the currently-not-used models (step S16) and thereby judges whether or not each of the estimated results from the currently-not-used models is correct (step S17).

When the estimated result from any of the currently-not-used models is correct (step S17: Yes), the evaluating function 352 increments the number of correct incidents of the currently-not-used model by 1 (step S18) and proceeds to step S19. On the contrary, when the estimated result from any of the currently-not-used models is incorrect (step S17: No), the evaluating function 352 immediately proceeds to step S19. Alternatively, in the mode in which the number of incorrect incidents is also counted, the process may proceed to step S19 after the number of incorrect incidents of the currently-not-used model is counted.

Subsequently, the evaluating function 352 judges whether or not the time so start the evaluation of the models has arrived (step S19). For example, when the models are to be evaluated every time a predetermined number (e.g., 100) of pieces of diagnosis result data have been registered, the evaluating function 352 determines that the time to perform the evaluation has not arrived, unless the predetermined number of pieces of diagnosis result data have been registered (step S19: No), and the process is returned to step S12.

On the contrary, when the predetermined number of pieces of diagnosis result data have been registered, the evaluating function 352 determines that the time to start the evaluation has arrived (step S19: Yes). On the basis of the counted result of the correct incidents of each of the models, the evaluating function 352 evaluates capabilities of each of the models by using an evaluation index such as a ratio of correct incidents (step S20), and the process is ended.

Figure 6:
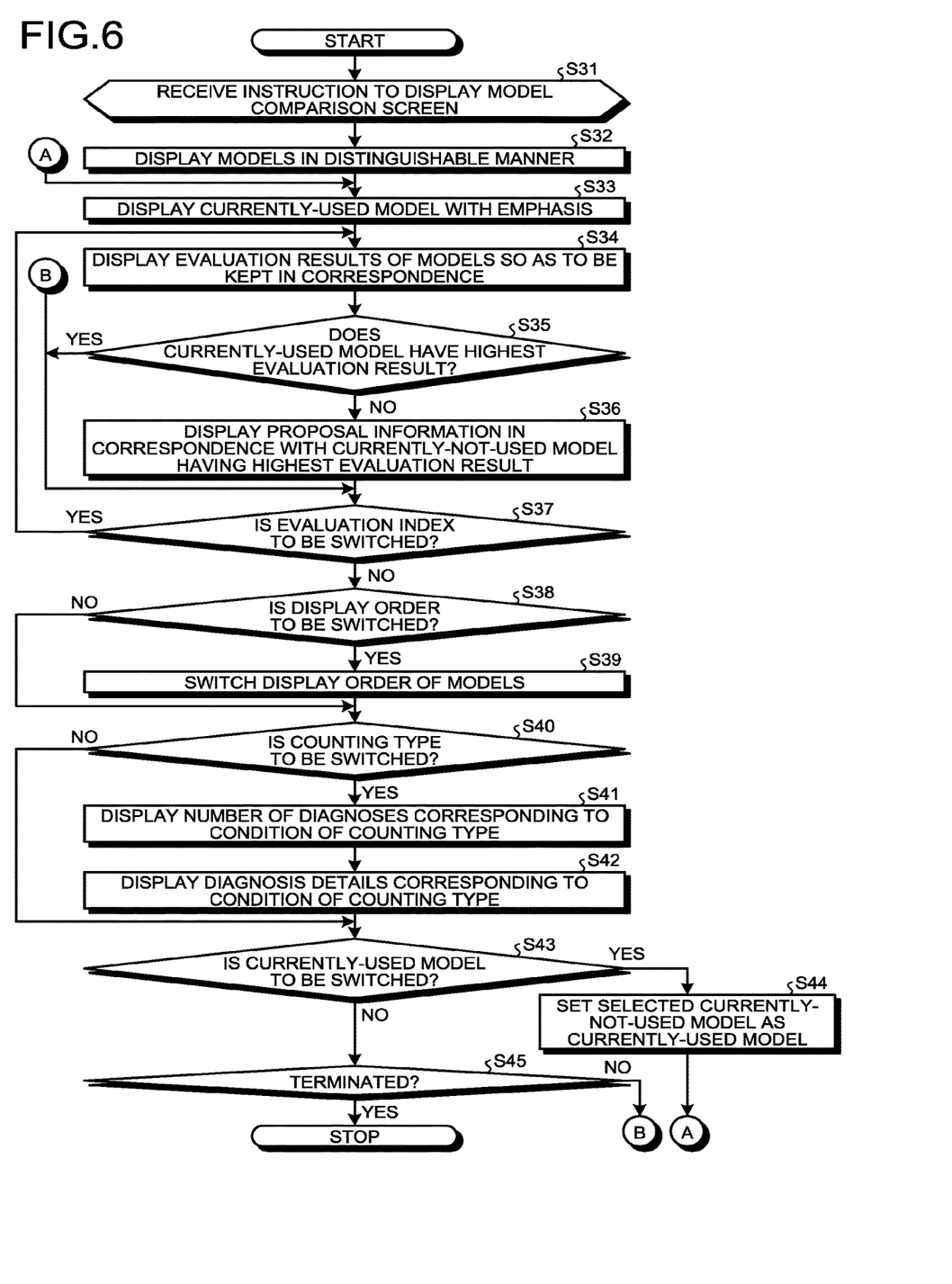
FIG. 6 is a flowchart illustrating an example of a model comparison screen display process performed by the data managing apparatus according to the embodiment.

FIG. 6 is a flowchart illustrating an example of a model comparison screen display process performed by the data managing apparatus 300. As a premise of the present process, it is assumed that the evaluation results of the models made by the evaluating function 352 have already been saved in the storage 302 or the like.

Upon receipt of a predetermined operation for instructing the display of the model comparison screen via the input interface 303 or the like (step S31), the display controlling function 354 causes the display 304 to display the models stored in the storage 302 in a distinguishable manner (step S32). Further, among the models displayed on the display 304, the display controlling function 354 displays the model set as the currently-used model with an emphasis (step S33).

Subsequently, on the basis of the evaluation results of the models derived by the evaluating function 352, the display controlling function 354 displays the evaluation results according to a selected evaluation index in correspondence with the respective models (step S34). In an initial display state, a default evaluation index (e.g., the ratio of correct incidents) and a default display order (e.g., "ascending order") are automatically selected.

Subsequently, the display controlling function 354 judges whether or not the model having the highest evaluation result is the currently-used model (step S35). When one of the currently-not-used models has the highest evaluation result (step S35: No), proposal information to propose that the currently-used model be switched is displayed in correspondence with the pertinent currently-not-used model (step S36), before the process proceeds to step S37. On the contrary, when the currently-used model has the highest evaluation result (step S35: Yes), the process immediately proceeds to step S37.

After that, the display controlling function 354 judges whether or not it is instructed via the input interface 303 or the like that the evaluation index be switched (step S37). When it is instructed that the evaluation index be switched (step S37: Yes), the display controlling function 354 returns the process to step S34 so as to display the evaluation results of the models by using the evaluation index selected to switch to. On the contrary, when it is not instructed that the evaluation index be switched (step S37: No), the process proceeds to step S38.

After that, the display controlling function 354 judges whether or not it is instructed via the input interface 303 or the like that the display order be switched (step S38). When it is instructed that the display order be switched (step S38: Yes), the display controlling function 354 switches the display so as to be in the display order selected to switch to (step S39) and proceeds to step S40. On the contrary, when it is not instructed that the display order be switched (step S38: No), the process immediately proceeds to step S40.

Subsequently, the display controlling function 354 judges whether or not it is instructed via the input interface 303 or the like that a counting type be selected (or switched) (step S40). When it is instructed that a counting type be selected (step S40: Yes), the display controlling function 354 displays, in the counted result display sections G11, the numbers of diagnoses corresponding to the condition of the selected counting type (step S41). Further, the display controlling function 354 displays, in the detail display sections G12, diagnosis details of the diagnoses corresponding to the condition of the counting type (step S42) and proceeds to step S43. On the contrary, when it is not instructed that a counting type be selected (step S40: No), the process proceeds to step S43. Further, in an initial display state, a default counting type (e.g., "only false negatives") may automatically be selected.

Subsequently, the setting function 353 judges whether or not it is instructed via the input interface 303 or the like that the currently-used model be switched (step S43). When it is instructed that the currently-used model be switched (step S43: Yes), the setting function 353 switches the currently-used model, by setting the selected currently-not-used model as a currently-used model (step S44) and subsequently, the process is returned to step S33. On the contrary, when it is not instructed that the currently-used model be switched (step S43: No), the process proceeds to step S45.

After that, the display controlling function 354 judges whether or not it is instructed via the input interface 303 or the like that the model comparison screen be terminated (step S45). When it is not instructed that the model comparison screen be terminated (step S45: No), the display controlling function 354 returns the process to step S37. On the contrary, when it is instructed that the model comparison screen be terminated (step S45: Yes), the display controlling function 354 ends the present process.

As explained above, in the present embodiment, each of the plurality of machine learning models is evaluated, on the basis of the output result from each of the machine learning models obtained by inputting mutually the same medical image data to the machine learning models and the success/failure judgment results on the output results, the plurality of machine learning models being created from the plurality of pieces of medical image data and are created from at least partially mutually-different medical image data. Further, in the present embodiment, the results of the evaluation on the machine learning models and the like are displayed in such a manner that comparison is possible. Accordingly, on the basis of the displayed screen (the model comparison screen), the user of the data managing apparatus 300 is able to easily compare the capabilities of the machine learning models, such as the evaluation results of the currently-used model and the currently-not-used models. Consequently, in the present embodiment, it is possible to provide an excellent environment for the user who performs the machine learning model selecting process.

The above embodiment may be carried out with modifications as appropriate, by changing a part of the configuration or the functions of the data managing apparatus 300. Thus, in the following sections, some modification examples of the above embodiment will be explained. The following explanations will primarily focus on differences from the above embodiment, and detailed explanations of certain aspects that have already been explained will be omitted. Further, the modification examples explained below may be carried out individually or may be carried out in combination as appropriate.

First Modification Example

In the above embodiment, the example was explained in which, with regard to the diagnoses using the global model GM, the model comparison screen displays the statistic results (the counted results and the evaluation results) from the host medical facility. However, because the global model GM uses the data from the plurality of medical facilities, it is desirable to offer the viewing of a list of the medical facilities that participated in the creation of the model. Accordingly, in the present modification example, a mode will be explained in which it is possible to display the list and the statistic results of the medical facilities that were involved in the creation of the global model GM.

According to a specific method, for example, the display controlling function 354 or the like at each of the medical facilities is configured to transmit or offer (disclose) evaluation results and counted results of the diagnoses made by using the global model GM at the host medical facility, to the other medical facilities involved in the creation of the global model GM. Accordingly, among the medical facilities involved in the creation of the global model GM, it is possible to mutually reference the evaluation results and the counted results of the diagnoses made by using the global model GM.

Further, it is desirable to enable each of the medical facilities to set one or both of the evaluation results and the counted results obtained at the medical facility to be undisclosed. In that situation, the evaluating function 352 exercises control so that it is impossible to reference the items set as "undisclosed" from the other medical facilities.

Figure 7:
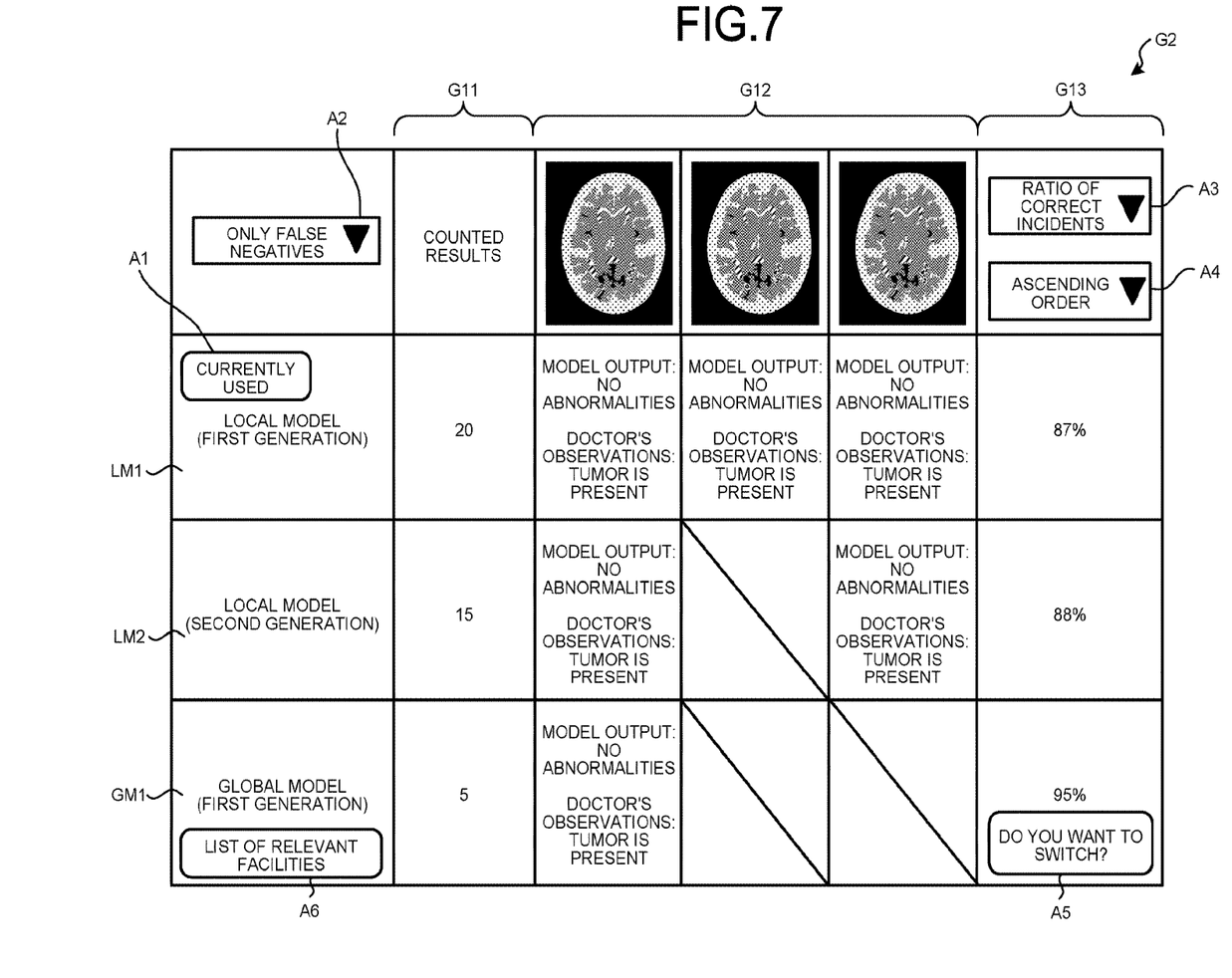
FIG. 7 is a drawing illustrating an example of a model comparison screen displayed by a display controlling function according to a first modification example.

FIG. 7 is a drawing illustrating an example of a model comparison screen displayed by the display controlling function 354 according to the present modification example. A model comparison screen G2 in FIG. 7 has the same screen configuration as that of the model comparison screen G1 explained with reference to FIG. 4. Further, as a difference from the model comparison screen G1, the display controlling function 354 according to the present modification example is configured to display an operator A6 for displaying information about the medical facilities involved in the creation of the global model GM1, so as to be kept in correspondence with the global model GM1.

Figure 8:
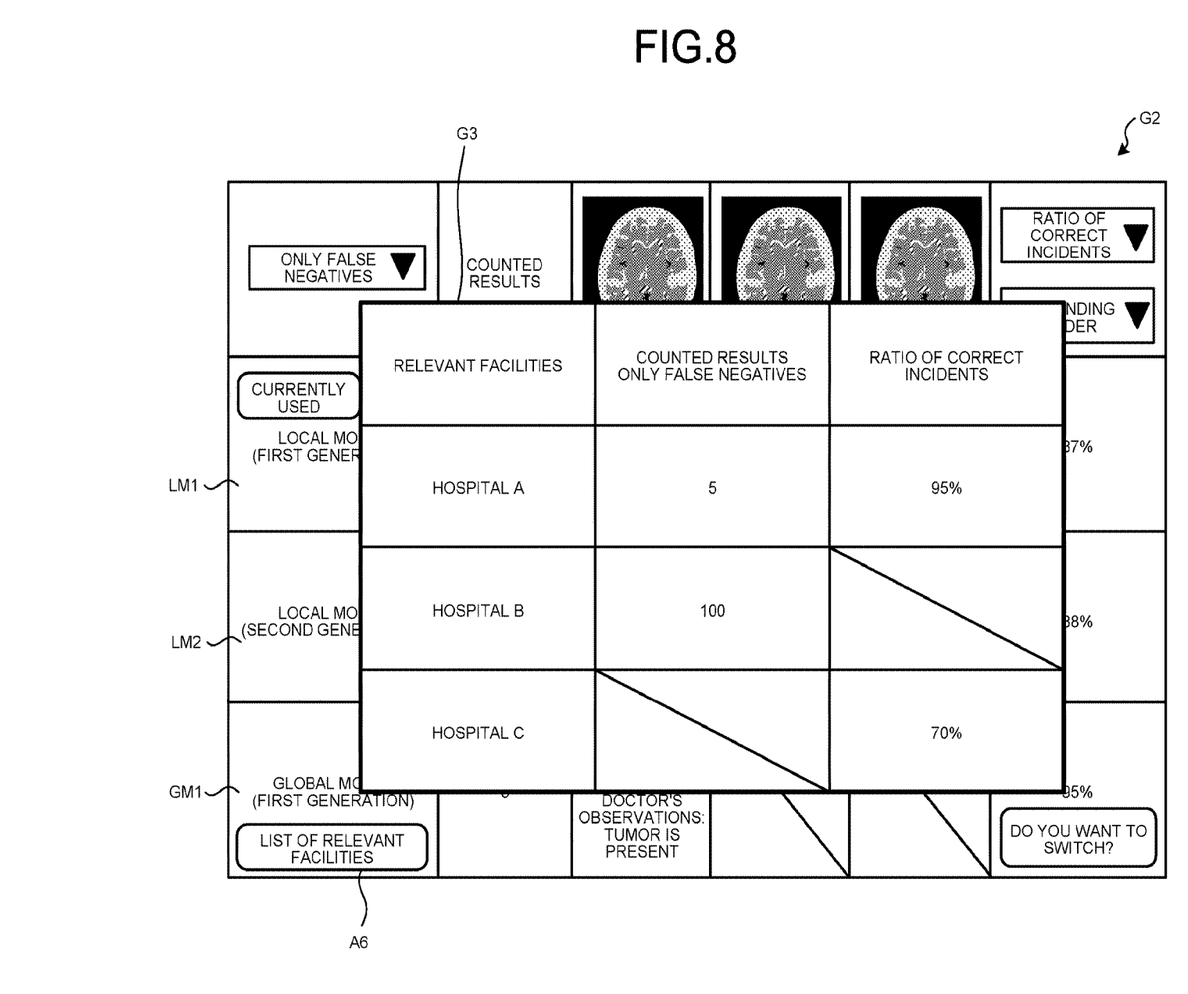
FIG. 8 is a drawing illustrating an example of a facility comparison screen displayed by the display controlling function according to the first modification example.

Upon receipt of an operation performed on the operator A6, the display controlling function 354 causes the display 304 to display, as illustrated in FIG. 8, a facility comparison screen G3 keeping the medical facilities involved in the creation of the global model GM1 in correspondence with evaluation results and counted results obtained at the medical facilities.

In the example in FIG. 8, hospital A, hospital B, and hospital C are displayed as the medical facilities involved in the creation of the global model GM1. In this situation, the display controlling function 354 may display the host medical facility (e.g., hospital A) with an emphasis. Further, as illustrated in FIG. 8, an evaluation result (the ratio of correct incidents) and a counted result (only false negatives) are displayed in correspondence with each of hospitals A, B, and C.

In this situation, any item that was set to be undisclosed by the medical facility being the source of the information is not displayed on the facility comparison screen G3. For example, because the ratio of correct incidents of hospital B and the counted result of hospital C are items that are set to be undisclosed by the respective medical facilities, the corresponding sections in the table are left empty.

As explained herein, because it is possible to reference the evaluation results and the like of the medical facilities involved in the creation of the global model GM1, the user of the data managing apparatus 300 is able to judge whether or not the global model GM1 is to be selected as a currently-used model, on the basis of the actual performances at the other hospitals and the like, for example. As a result, according to the present modification example, it is possible to assist the machine learning model selecting process.

In the above embodiment, the example was explained in which the selecting process is performed on the machine learning models created by using the medical image data; however, possible embodiments are not limited to this example. The present disclosure is also applicable to machine learning models created from medical data other than medical image data.

Second Modification Example

In the above embodiment, the example was explained in which the evaluation is made on the plurality of machine learning models created from the pieces of medical image data that are at least partially different; however, possible examples of the machine learning models subject to the evaluation are not limited to those described in the above embodiment. It is also possible to evaluate a plurality of machine learning models created under mutually-different conditions. For example, an evaluation may be made on a plurality of machine learning models created under mutually-different parameter conditions such as hyperparameters. In that situation, the evaluation may be made on the plurality of machine learning models created by using the mutually-different parameter conditions, on the basis of mutually the same data set (medical image data and diagnosis results). Consequently, according to the present modification example, it is possible to efficiently select a suitable machine learning model from among the machine learning models created under various conditions.

Third Modification Example

In the above embodiment, the example was explained in which the medical image data is used as the medical data related to the creation of the machine learning model; however, possible embodiments are not limited to this example. Even when the machine learning models are created by using other types of medical data, it is possible to assist the machine learning model selecting process by using the same method as that described in the above embodiment.

Fourth Modification Example

In the above embodiment, the data managing apparatus 300 is configured to include the acquiring function 351, the evaluating function 352, the setting function 353, and the display controlling function 354; however, these functions may be included in another apparatus different from the data managing apparatus 300.

For example, another apparatus such as the medical image managing system 200 may include the abovementioned functions. Further, the data managing apparatus 300 may be configured, for example, to cause a display device of any of the terminal apparatus 400 to display the abovementioned various types of screens in the form of a web service or the like. Further, the data managing apparatus 300 does not necessarily have to be configured with a single computer device and may be realized by using a plurality of computer devices connected to a network. In that situation, each of the computer devices may include one or more of the abovementioned functions so that, as a whole, the medical information processing apparatus is realized.

In the embodiments described above, the example was explained in which the evaluating unit and the display controlling unit of the present disclosure are realized by the acquiring function 351, the evaluating function 352, the setting function 353, and the display controlling function 354 of the processing circuitry 305; however, possible embodiments are not limited to this example. For instance, the evaluating unit and the display controlling unit of the present disclosure may be configured to realize the functions by using only hardware or a combination of hardware and software.

Further, the term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The processor realizes the functions by reading and executing the programs saved in the storage 302. Further, instead of saving the programs in the storage 302, it is also acceptable to directly incorporate the programs into the circuitry of the processor. In that situation, the processor realizes the functions by reading and executing the programs incorporated in the circuitry thereof. Moreover, the processor of the present embodiments do not necessarily have to be structured as a single circuit. It is also acceptable to structure one processor by combining together a plurality of independent circuits so as to realize the functions thereof.

The programs executed by the processor are provided as being incorporated, in advance, in a Read Only Memory (ROM), a storage, or the like. The programs may be provided as being recorded on a computer-readable storage medium such as a Compact Disk Read-Only Memory (CD-ROM), a Flexible Disk (FD), a Compact Disk Recordable (CD-R), Digital Versatile Disk (DVD), or the like, in a file in a format that is installable or executable by these devices. Further, the programs may be stored in a computer connected to a network such as the Internet so as to be provided or distributed as being downloaded via the network. For example, the programs are structured with modules including the functional units described above. In the actual hardware, as a result of a CPU reading and executing the programs from a storage medium such as a ROM, the modules are loaded into a main storage device and generated in the main storage device.

According to at least one aspect of the embodiments and the modification examples described above, it is possible to assist the machine learning model selecting process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
processing circuitry configured to
evaluate each of a plurality of machine learning models by obtaining a corresponding output result from each of the plurality of machine learning models by inputting mutually identical medical data to each of the plurality of machine learning models, and by obtaining success/failure judgment results on the output results, the plurality of machine learning models having been created from a plurality of pieces of medical data, and either created from at least partially mutually-different medical data or created under mutually-different parameter conditions;
display a result of the evaluation of each of the plurality of machine learning models in such a manner that comparison is possible; and
when an output result among the obtained output results from the plurality of machine learning models corresponds to a designated condition, display, in association with one another, (i) the output result corresponding to the designated condition, (ii) a piece of medical data from which the output result corresponding to the designated condition has been obtained, and (iii) a result of diagnosis made by a medical doctor from the piece of medical data from which the output result corresponding to the designated condition has been obtained.

2. The medical information processing apparatus according to claim 1, wherein, based on the output result from one of the plurality of machine learning models and the result of diagnosis made by the medical doctor from the piece of medical data from which the output result corresponding to the designated condition has been obtained, the processing circuitry is further configured to determine a success/failure of the output results from one or more other machine learning models of the plurality of machine learning models.

3. The medical information processing apparatus according to claim 1, wherein, among the output results output from the plurality of machine learning models, the processing circuitry is further configured to display a quantity of output results corresponding to the designated condition for each of the plurality of machine learning models.

4. The medical information processing apparatus of claim 1, wherein the processing circuitry is further configured to:
    display a user interface element allowing a user to select a counting type of a plurality of counting types;
    receive, from the user, an input of a particular counting type selected via the displayed user interface element; and
    display the result of the evaluation of each of the plurality of machine learning models only for the particular selected counting type.

5. The medical information processing apparatus of claim 4, wherein the processing circuitry is further configured to display the user interface element allowing the user to select the counting type of the plurality of counting types, which include at least two of all, only correct incidents, only false negatives, and only false positives.

6. The medical information processing apparatus according to claim 1, wherein the plurality of machine learning models evaluated by the processing circuitry include a first machine learning model created from the plurality of pieces of medical data obtained at a mutually same medical facility.

7. The medical information processing apparatus according to claim 1, wherein the plurality of machine learning models evaluated by the processing circuitry include a second machine learning model created from the plurality of pieces of medical data obtained at a plurality of medical facilities.

8. The medical information processing apparatus according to claim 7, wherein the processing circuitry is further configured to display information about each of the plurality of medical facilities related to the creation of the second machine learning model.

9. The medical information processing apparatus according to claim 7, wherein the processing circuitry is further configured to display the results of the evaluation on the second machine learning model made at the plurality of medical facilities related to the creation of the second machine learning model in such a manner that comparison is possible.

10. The medical information processing apparatus according to claim 9, wherein the processing circuitry is further configured to control the display of the results of the evaluation on the second machine learning model, based on a setting established in advance as to whether the results of the evaluation on the second machine learning model are to be disclosed or undisclosed.

11. A medical information processing method, comprising:
    evaluating each of a plurality of machine learning models by obtaining an output result from each of the plurality of machine learning models by inputting mutually identical medical data to the plurality of machine learning models, and by obtaining success/failure judgment results on the output results, the plurality of machine learning models having been created from a plurality of pieces of medical data, and either created from at least partially mutually-different medical data or created under mutually-different parameter conditions;
    displaying a result of the evaluation of each of the plurality of machine learning models in such a manner that comparison is possible; and
    when an output result among the obtained output results from the plurality of machine learning models corresponds to a designated condition, displaying, in association with one another, (i) the output result corresponding to the designated condition, (ii) a piece of medical data from which the output result corresponding to the designated condition has been obtained, and (iii) a result of diagnosis made by a medical doctor from the piece of medical data from which the output result corresponding to the designated condition has been obtained.

* * * * *